United States Patent [19]
Alt

[11] Patent Number: 6,159,142
[45] Date of Patent: *Dec. 12, 2000

[54] STENT WITH RADIOACTIVE COATING FOR TREATING BLOOD VESSELS TO PREVENT RESTENOSIS

[75] Inventor: Eckhard Alt, Ottobrunn, Germany

[73] Assignee: InFlow Dynamics, Inc., Wilmington, Del.

[ * ] Notice: This patent is subject to a terminal disclaimer.

[21] Appl. No.: 09/186,574

[22] Filed: Nov. 5, 1998

Related U.S. Application Data

[63] Continuation-in-part of application No. 08/762,739, Dec. 10, 1996, Pat. No. 5,871,437.

[51] Int. Cl.⁷ ..................................................... A61N 5/00
[52] U.S. Cl. ............................................................... 600/3
[58] Field of Search ........................... 600/1–8; 606/108, 606/191–98; 128/897–898

[56] References Cited

U.S. PATENT DOCUMENTS

| | | | |
|---|---|---|---|
| 5,059,166 | 10/1991 | Fischell et al. .............................. | 600/3 |
| 5,871,437 | 2/1999 | Alt ............................................. | 600/3 |
| 5,919,126 | 7/1999 | Armini ....................................... | 600/3 |
| 5,942,209 | 8/1999 | Leavitt et al. ............................... | 600/7 |

*Primary Examiner*—Cary O'Connor
*Assistant Examiner*—Catherine McPherson

[57] ABSTRACT

A non-radioactive metallic stent is coated with a biodegradable thin coating of less than about 100 microns in thickness selected to avoid provoking any foreign body reaction. The biodegradable material in the coating disintegrates over time in the presence of body fluid. The coating contains a radioactive source of, for example, a beta radiation emitter for irradiation of tissue when the stent is implanted in a blood vessel treated by angioplasty, to inhibit proliferation of smooth muscle cells in response to trauma to the wall of the blood vessel from the angioplasty, and thereby to prevent rapid tissue growth and consequent restenosis of the vessel. The stent coating incorporating the radioactive source constitutes a first layer adherent to and overlying the surface of the stent. The coating may further include a second layer atop the first layer, incorporating an anti-coagulant substance to inhibit thrombus formation on the stent. The radioactive source has an activity level of, for example, approximately one microcurie, and a half life which is shorter than the time interval required for the biodegradable coating to completely disintegrate. Thus, by the time the coating disappears, the effective level of radioactivity of the radioactive substance has dissipated to an extent which avoids any lingering systemic effect.

21 Claims, 1 Drawing Sheet

STENT WITH RADIOACTIVE COATING FOR TREATING BLOOD VESSELS TO PREVENT RESTENOSIS

CROSS-REFERENCE TO RELATED APPLICATION

This application is a continuation-in-part of co-pending patent application Ser. No. 08/762,739 of the same inventor and assignee, filed Dec. 10, 1996 now U.S. Pat. No. 5,871,437.

BACKGROUND OF THE INVENTION

The present invention relates generally to stents for implantation in a body to maintain the lumen of a duct or vessel open for unimpeded passage of liquid, solid or gas therethrough. For example, stents are typically implanted to prevent collapse or to impede narrowing of a blood vessel such as a coronary artery, so that blood will continue to flow freely through the vessel after an occlusion has been found and/or an angioplasty procedure has been performed, but stents may also be implanted in other body ducts for a similar purpose of allowing other body fluids or solid material to pass through the duct. More particularly, the present invention is directed to stents which are rendered radioactive prior to implantation to inhibit the formation or reformation of a stenotic region or to reduce the rate of growth of a tumor that otherwise would occlude a duct.

The benefits of angioplasty, particularly percutaneous transluminal coronary angioplasty (PTCA) and most especially balloon angioplasty, has been amply demonstrated over more than a decade. Angioplasty is an effective procedure to open blood vessels which have been partly or even fully occluded by a stenotic region such as a buildup of plaque or fatty deposits on the inner lining. Left untreated, such deposits in the coronary arteries could result in myocardial infarction and death. Blockage occurring in other blood vessels may lead to maladies such as phlebitis, paralysis or atrophy, for example.

With PTCA patients, however, it was found that restenosis occurs in as much as 50% of the cases, typically within only a few weeks or months following the initial procedure. A repeat procedure in such cases often demonstrated little or no effect. It was discovered that the restenosis was usually attributable not to new deposits of plaque or to thrombus formation, but rather to a response of the tissue to trauma that resulted from the angioplasty procedure itself, even the rather mild trauma induced by balloon angioplasty in contrast to laser or scraping techniques. Contact with the inner lining of the vessel wall induces a form of cellular hyperplasia manifested by a profound proliferation of the smooth muscle cells, to an extent that reocclusion may even exceed the clogging that prompted resort to the original angioplasty procedure. Production of the new tissue cells occurs within the intimal and medial layers, in a mechanism analogous to wound healing and scar tissue.

To reduce the likelihood of reocclusion of the vessel, it has become common practice for the physician to implant a stent in the patient at the site of the angioplasty or atherectomy procedure, immediately following that procedure, as a prophylactic measure. The stent is advanced on a balloon catheter to the designated site of the prior (or even contemporaneous) procedure under fluoroscopic observation. When the stent is positioned at the proper site, the balloon is inflated to expand the stent radially to an inner diameter at or slightly larger than the normal unobstructed inner diameter of the arterial wall, for permanent retention at the site. The stent implant procedure from the time of initial insertion to the time of retracting the balloon is relatively brief, and certainly far less invasive than coronary bypass surgery.

Despite its considerable benefits, coronary stenting alone is not a panacea, as studies have shown that about 30% of the patient population subjected to that procedure will still experience restenosis. Clearly, that percentage is still quite favorable compared to the approximate 50% recurrence rate for patients who have had a PTCA procedure without stent insertion at the angioplasty site. But improvement is needed. Also, risks of inflammation of the vessel wall and of attachment of thrombi at the site are exacerbated by the very presence of the stent in the vessel.

A stent is typically composed of a biologically compatible material (biomaterial) such as a biocompatible metal wire mesh of tubular shape or a metallic tube populated with sidewall through-holes to permit radial expansion thereof. The stent should be of sufficient strength and rigidity to maintain its shape after deployment, and to resist the normal elastic recoil of the artery that occurs after the vessel wall has been stretched. After the stent is inserted into the vessel, its presence in the blood stream may induce a local or even systemic activation of the patient's hemostase coagulation system. When stents are used in blood vessels of less than about 3 millimeters (mm) diameter, such as the coronary arteries, the incidence of complications increases to an even greater extent.

In the past several years, considerable research has been devoted worldwide to studying the mechanisms of restenosis. Research conducted by the applicant has indicated that local thrombus formation is one of the mechanisms that promote restenosis. Animal research by the applicant has shown that a further 30% reduction in the restenosis rate (i.e., the rate of recurrence) may be achieved if the stent is coated with a biocompatible, non-foreign body-inducing, biodegradable polylactic acid of thin paint-like thickness in a range below 100 microns, and preferably about 10 microns thick. This thin coating on a metallic stent may be used to release drugs incorporated therein, such as hirudin and/or a platelet inhibitor such as prostacyclin ($PGI_2$), a prostaglandin. Both of these drugs are effective to inhibit proliferation of smooth muscle cells, and decrease the activation of the intrinsic and extrinsic coagulation system. Therefore, the potential for a very significant reduction in restenosis has been demonstrated in these animal experiments.

That invention is disclosed in co-pending patent application Ser. No. 08/798,333, now U.S. Pat. No. 5,788,979, of the applicant herein. The stent is coated with a biodegradable substance or composition which undergoes continuous degradation in the presence of body fluids such as blood, to self-cleanse the surface as well as to release thrombus inhibitors incorporated in the coating. Disintegration of the carrier occurs slowly through hydrolytic, enzymatic or other degenerative processes. The biodegradable coating acts to prevent the adhesion of thrombi to the biomaterial or the coating surface, especially as a result of the inhibitors in the coating, which undergo slow release with the controlled degradation of the carrier. Blood components such as albumin, adhesive proteins, and thrombocytes can adhere to the surface of the biomaterial, if at all, for only very limited time because of the continuous cleansing action along the entire surface that results from the ongoing biodegradation.

Materials used for the biodegradable coating and the slow, continuous release of drugs incorporated therein include synthetic and naturally occurring aliphatic and hydroxy polymers of lactic acid, glycolic acid, mixed polymers and blends. Alternative materials for those purposes include biodegradable synthetic polymers such as polyhydroxybutyrates, polyhydroxyvaleriates and blends, and polydioxanon, modified starch, gelatine, modified cellulose, caprolactaine polymers, acrylic acid and methacrylic acid and their derivatives. It is important that the coating have tight adhesion to the surface of the biomaterial, which can be accomplished by applying the aforementioned thin, paint-like coating of the biodegradable material that may have coagulation inhibitors blended therein, as by dipping or spraying, followed by drying, before implanting the coated biomaterial device.

Two or more different drugs suitable for inhibiting coagulation may be incorporated into the carrier to provide a synergistic effect with release as the coating slowly disintegrates, as where one substance inhibits plasmatic coagulation and another inhibits platelet-induced, cellular coagulation. Hyperplasia is inhibited or suppressed as well, and infection is avoided even when the coating is applied to the biomaterial under non-aseptic conditions.

Hirudin is a naturally occurring and potent thrombin inhibitor that may be incorporated into the carrier with very beneficial results. Similar results are achievable with natural or synthetic prostaglandin derivative instead of or in addition to the hirudin. Specific platelet inhibitors that act on the GP IIb/IIIa receptor are especially helpful in preventing platelet activation following coronary interventions. Anti-adhesive peptides are also suitable, especially with thrombocyte aggregation inhibitors. Inhibition of adhesive proteins which function as bridging proteins tends to preclude adhesion and aggregation of thrombocytes. Locally effective, naturally occurring fibrinolytic substance such as Urokinase, r-TPA or Streptokinase, when added to the coating carrier for slow release, enhance continuous self-cleaning of the surface.

Anti-proliferation substances may be incorporated into the coating carrier to slow proliferation of smooth muscle cells at the internal surface of the vascular wall. Such substances include corticoids and dexamethasone, which prevent local inflammation and further inducement of clotting by mediators of inflammation. Substances such as taxol, tamoxifen and other cytostatic drugs directly interfere with intimal and medial hyperplasia, to slow or prevent restenosis, especially when incorporated into the coating carrier for slow release during biodegradation. Local relaxation of a vessel can be achieved by inclusion of nitrogen monoxide (NO) or other drugs that release NO, such as organic nitrates or molsidomin, or SIN1, its biologically effective metabolite.

A slow release of appropriate drugs incorporated in the biodegradable coating can serve to prevent thrombus formation and also to inhibit inflammatory responses and restenosis of a coronary artery in which a stent is implanted. In this respect, another factor that contributes to restenosis is the natural elastic recoil of the artery and resulting loss of lumen diameter that follows an angioplasty procedure. Stenting serves to stabilize the artery and to resist this natural recoil, by virtue of the rigid structure of the metal stent in its expanded state.

The amount and dosage of the drug or combination of drugs incorporated into and released from the biodegradable carrier material is adjusted to produce a local suppression of the thrombotic and restenotic processes, while allowing systemic clotting of the blood. The active period of the coated stent may be adjusted by varying the thickness of the coating, the specific type of biodegradable material selected for the carrier, and the specific time release of incorporated drugs or other substances selected to prevent thrombus formation or attachment, subsequent restenosis and inflammation of the vessel.

The biodegradable coating undergoes virtually complete disintegration during an initial period of from two weeks to about three months following implantation of the stent. By that time the mechanisms that promote restenosis will have subsided, and a natural tissue layer of limited extent will have begun to form on the stent. This acute response is deemed to be most important, substantially lessening a need for more long-term action. In a study conducted by the applicant, fully four weeks after implantation of a coated stent in a coronary artery of a sheep the device was found to be unobstructed and to have kept the artery fully open for blood flow therethrough, whereas an uncoated stent implanted at the same time displayed a considerably reduced lumen diameter.

The biodegradable coating may also be applied to the stent in multiple layers, either to achieve a desired thickness of the overall coating or a portion thereof for prolonged action, or to employ a different beneficial substance or substances in each layer to provide a desired response during a particular period following implantation of the coated stent. For example, at the moment the stent is introduced into the vessel, thrombus formation will commence, so that a need exists for a top layer if not the entire layer of the coating to be most effective against this early thrombus formation, with a relatively rapid release of the incorporated, potent anticoagulation drug to complement the self-cleansing action of the disintegrating carrier. For the longer term of two weeks to three months after implantation, greater concern resides in the possibility of intimal hyperplasia that can again narrow or fully obstruct the lumen of the vessel. Hence, the same substance as was present or a different substance from that in the top layer might be selected for use in the application of the coating to meet such exigencies. Hirudin, for example, can be effective against both of these mechanisms or phenomena.

The prior art has suggested the use of radiation to inhibit restenosis. Fischell et al. proposes in U.S. Pat. No. 4,768,507 the use of a special percutaneous insertion catheter for purposes of enhancing luminal dilatation, preventing arterial restenosis, and preventing vessel blockage resulting from intimal dissection following balloon and other methods of angioplasty.

In U.S. Pat. No. 4,779,641 and co-pending European patent application No. 92309580.6, the use of an interbiliary duct stent is disclosed. There, radioactive coils of a wire which are embedded into the interior wall of the bile duct ostensibly to prevent restenotic processes from occurring.

U.S. Pat. No. 4,448,691 and co-pending European patent application No. 90313433.6 disclose a helical wire stent, provided for insertion into an artery following balloon angioplasty or atherectomy, which incorporates or is plated with a radioisotope. According to that patent, a radioactive stent will decrease the proliferation of smooth muscle cells. The disclosure teaches that the stent may be made radioactive by irradiation or by incorporating a radioisotope into the material of which the stent is composed. Another solution would be to locate the radioisotope at the core of the tubular stent or to plate the radioisotope onto the surface of the stent. The patent also teaches, aside from the provision of radioactivity of the stent, that an outer coating of anti-thrombogenic material might be applied to the stent.

U.S. Pat. No. 5,059,166 to Fischell et al. discloses a helical coil spring stent composed of a pure metal which is made radioactive by irradiation. Alternative embodiments disclosed in summary fashion in the patent include a steel helical stent which is alloyed with a metal that can be made radioactive, such as phosphorus (14.3 day half life); or a helical coil which has a radioisotope core and a spring material covering over the core; or a coil spring core plated with a radioisotope such as gold 198 ($Au^{198}$, which has a half life of 2.7days), which may be coated with an anti-thrombogenic layer of carbon.

Clinical basic science reports such as "Inhibition of neointimal proliferation with low dose irradiation from a beta particle emitting stent" by John Laird et al published in Circulation (93:529–536, 1996) describe creating a beta particle-emitting stent by bombarding the outside of a titanium wire with phosphorus. The implantation of phosphorus into the titanium wire was achieved by placing the $P^{31}$ into a special vacuum apparatus, and then vaporizing, ionizing and, accelerating the ions with a higher voltage so that the $P^{31}$ atoms become buried beneath the surface of the titanium wire in a thickness of about ⅓ micron. After exposing the wire together with the phosphorus radioisotope for several hours to a flux of slow neutrons part of the $P^{31}$ atoms were converted into a $P^{32}$, a pure beta particle emitter with a maximum energy of 1.709 megaelectron-volts, an average of 0.695 megaelectron-volts, and a half-life of 14.6 days.

Despite the convincing clinical results obtained by this method, practical application of the method in human patients raises considerable concerns. First, it is difficult to create a pure beta emitter from phosphorus if a stent is exposed to a flux of slow neutrons. In addition to converting phosphorus from $P^{31}$ to $P^{32}$, the metallic structure of the titanium wire will become radioactive. Therefore, about 20 days are needed to allow the radiation to decay, especially gamma radiation which originates from the titanium wire. Even worse is the situation where a metal such as stainless steel undergoes radioactive irradiation, resulting in production of unwanted γ radiation and a wide range of short and long term radionuclei such as $cobalt^{57}$, $iron^{55}$, $zinc^{65}$, $molybdenum^{99}$, $cobalt^{55}$. A pure beta radiation emitter with a penetration depth of about 3 millimeters is clearly superior for a radioactive stent for purposes of local action, side effects, and handling.

Reports have indicated that good results have been obtained with a radioactive wire inserted into the coronary arteries or into arteriosclerotic vessels of animals. Results obtained with a gamma radiation source from a wire stems from the deeper penetration of gamma radiation, which is about 10 mm. Assuming that the vessel is 3 to 4 mm in diameter, a distance of 2 to 4 mm depending on the actual placement of the wire toward a side wall has to be overcome before the radiation acts. Therefore, the clinical results that have been obtained with radioactive guide wires that have been inserted into the coronary arteries for a period ranging from about 4 to 20 minutes for delivery of a total dosage of about 8 to 18 Gray (Gy) have shown that gamma radiation has a beneficial effect while beta radiation from a wire is less favorable. On the other hand, gamma radiation which originates from a stainless steel stent such as composed of 316L is less favorable since the properties of β radiation such as a short half-life and a short penetration depth are superior to γ radiation originating from radioactive 316L with a long half-life and a deeper penetration since the proliferative processes of smooth muscle cell proliferation occur within the first 20 to 30 days and only in the very close vicinity of the stent.

In addition, a half-life which is too short such as one to two days considerably impacts on logistics if a metallic stent needs to be made radioactive. That is, by the time the stent is ready for use, its radioactivity level may have decayed to a point which makes it unsuitable for the intended purpose.

A discussion of the irradiation of nickel-titanium or steel is found in German patent P 4315002 issued to Christoff, and corresponding PCT application EP 94-01373 which corresponds to EP 94 916177.2, reporting on a metallic stent with a short and a long half-life.

While the prior art reports on various ways to make a metallic stent radioactive, for the purpose of practical use it is assumed that the availability of a non-radioactive metallic stent has considerable advantages. It is a principal aim of the present invention to provide a method to provide radioactivity without incorporating the radioactive material into a metallic stent or irradiating the stent itself. In this way, the radioactivity can be more easily integrated, manufactured, maintained, controlled, distributed, and so forth, than is possible with a radioactive metallic stent that is produced by the usual known methods.

SUMMARY OF THE INVENTION

The present invention employs a radioisotope or a material which can be made radioactive, preferably but not necessarily a beta emitter, examples being phosphorus 32 ($P^{32}$) or gold 198 ($Au^{198}$) but other materials such as those mentioned earlier herein may alternatively be used.

According to the invention, a metallic stent is coated with a biodegradable or non-biodegradable coating or carrier which incorporates a beta emitting radioactive source such as phosphorus $P^{32}$ with a radioactivity level of about one microcurie. Preferably, phosphorus in organic form is obtained for low level radiation test purposes in a microcurie range, and can be easily blended into a chloroform or solvent of a polylactic carrier. In addition, not only is the restenosis triggered by proliferation of smooth muscle cells inhibited, but the restenosis triggered by thrombus formation can also be inhibited, by incorporating into the coating carrier not only a radioactive material such as a phosphorus isotope, but also hirudin or iloprost or other anti-coagulant.

To prevent the phosphorus radioactivity from being distributed throughout the body, it is preferred that an inner coating containing the radioactive phosphorus be applied directly onto the surface of the stent, and then an outer coating applied atop the inner coating, containing substances such as an anti-coagulant or a proliferation inhibitor such as taxol or other hemotherapeutics. Thus, an important aspect of the invention is that the coating may be applied in multiple layers to accomplish this task, each of which is allowed to dry before the next is applied.

Another important aspect of the invention is that a combination of a cytostatic substance such as taxol and radiation is beneficial because the presence of the cytostatic substance causes the cell proliferation to be more organized in a certain phase that makes it more susceptible to radiation. For example, exposure to radioactivity in the presence of the cytostatic substance provides the same effect at 20% of the delivered dosage as would 100% radioactivity (i.e., with no cytostatic or comparable substance present).

Preferably, the coating or carrier material is biodegradable, and the half life of the radioactive emitter (preferably but not necessarily a beta emitter) is selected to be shorter than the degradation rate of the biodegradable carrier for the thickness of the coating involved, that is, shorter than the time interval that the layer in which the radioactive source material is incorporated will completely disintegrate. Also, the radioactive emitter is selected to have an activity level that will assure delivery of sufficient radioactivity to the tissue at the inner lining of the coronary artery (for example) to achieve the desired purpose. Consequently, the tissue in the locality of the vascular site targeted for treatment will receive a radiation dosage sufficient to inhibit cellular proliferation, and thus, restenosis of the vessel at the site of the trauma before a complete degradation or disintegration of the carrier. Additionally, the continuing and complete disintegration of the carrier will not result in a systemic distribution of particulate matter of measurable radioactivity level throughout the body of the patient.

BRIEF DESCRIPTION OF THE DRAWINGS

The above and still further aims, objects, features, aspects and attendant advantages of the present invention will become apparent from the following detailed description of certain preferred compositions, structures and methods of fabrication constituting the best mode presently contemplated of practicing the invention, when taken in conjunction with the accompanying drawings, in which.

DETAILED DESCRIPTION OF THE PREFERRED EMBODIMENTS AND METHODS

Preferably, the coating to be applied to a stent according to the present invention employs a biodegradable carrier which is selected to undergo a slow disintegration without harmful effect in the cardiovascular system. Such a coating carrier serves to continuously cleanse the exposed surface of the stent by removal of a microscopically thin layer of the carrier material while releasing selected drugs incorporated therein. The carrier may be selected from natural or synthetic aliphatic or hydroxy polymers of lactic acid, glycolic acid, or mixed polymers or blends thereof or from synthetic polymers such as polyhydroxybutyrates, polyhydroxyvaleriates or blends thereof, or from polydioxanon, modified starch, gelatine, modified cellulose, caprolactaine polymers, acrylic acid or methacrylic acid or their derivatives. Alternatively, a non-biodegradable carrier may be used. A peripheral primary requirement for either such carrier is that it be sufficiently elastic and flexible to remain unruptured on the exposed surfaces of the stent despite a considerable expansion of the stent during deployment to increase the lumen diameter from, typically, 1 mm to 5 mm.

A substance which may comprise a single drug or agent, such as hirudin or a platelet inhibitor such as prostacyclin ($PGI_2$), or a proliferation inhibitor such as taxol or other hemotherapeutics is incorporated into the carrier. Each of these is effective to inhibit proliferation of smooth muscle cells, and decrease the activation of the intrinsic and extrinsic coagulation system. Alternatively, a synergistic combination of agents of sufficient potency to prevent the thrombus formation, inflammation and restenosis of the vessel, can be blended into the carrier prior to application to the stent. In the preferred method, the coating containing these types of drugs is applied as the outer layer, atop an inner layer to be applied directly to the stent surface and incorporating the radioactive material such as $P^{32}$ with a radioactivity level of about one microcurie. The additive drugs or substances for the outer layer of the coating should be capable of being dissolved or dispersed in a quickly evaporating solution, such as chloroform or methyl chloride, to effect fast drying with a low boiling point.

Figure 1:
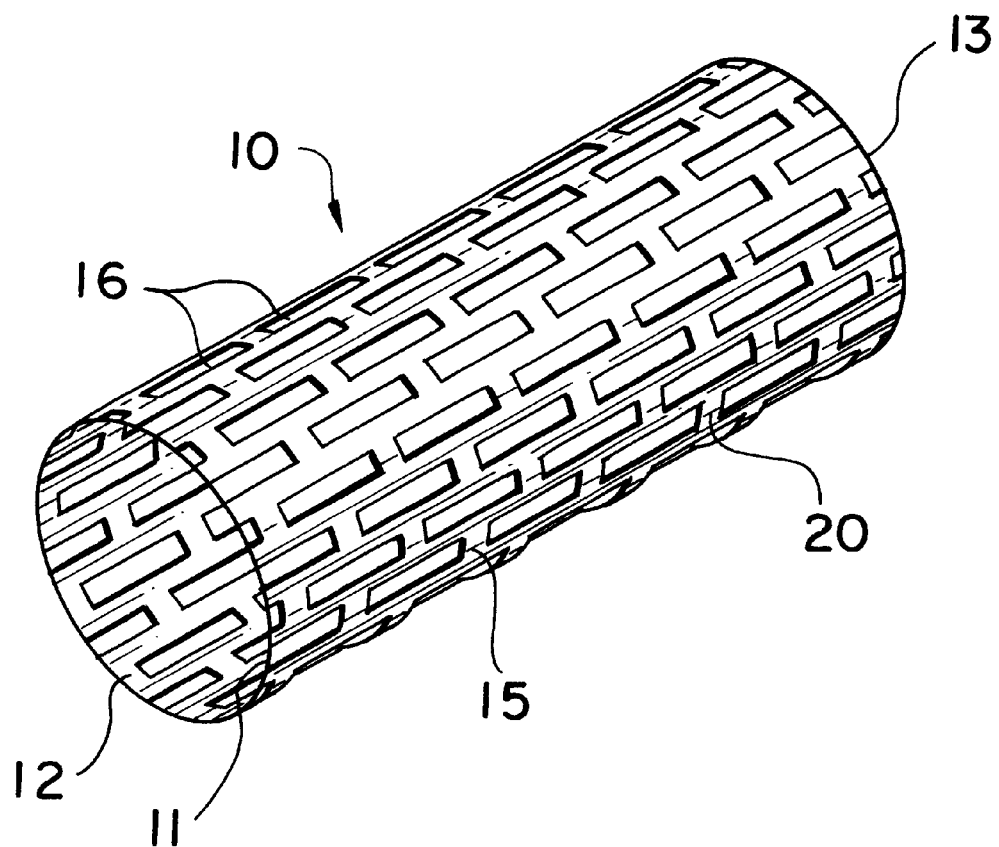
FIG. 1 is a partly complete perspective view of an example of a vascular stent in which the present invention is employed.

Referring to the Figures, the carrier should adhere tightly to the surface of the metal (or non-metallic) stent 10, and preferably this is accomplished by applying the carrier material in successive thin layers. The stent 10 itself is preferably an non-radioactive biocompatible metallic tube (e.g., 316L stainless steel with or without a further biocompatible metal coating) 11 with open ends 12 and 13, and whose sidewall 15 is populated throughout with through-holes 16, or alternatively a metal tubular wire mesh. Although only a few through-holes are shown in FIG. 1, it will be understood that they are present throughout the sidewall. Stent structures are well known and the particular structure of the stent is not a factor in the present invention, so it is not necessary to go into further detail. Suffice it to say that the carrier coating 20 is preferably applied to the entire exposed surface of the stent, but alternatively may be limited to a particular portion of the stent surface if desired, and in any event should not applied in a manner that will lead to blockage of through holes or mesh openings in the stent. Even if the latter were to occur, however, it would not interfere with the capability to open the stent at the time it is to be deployed, typically by inflating the balloon catheter on which the stent is mounted to expand its diameter to engage the inner lining of the blood vessel.

Figure 2:
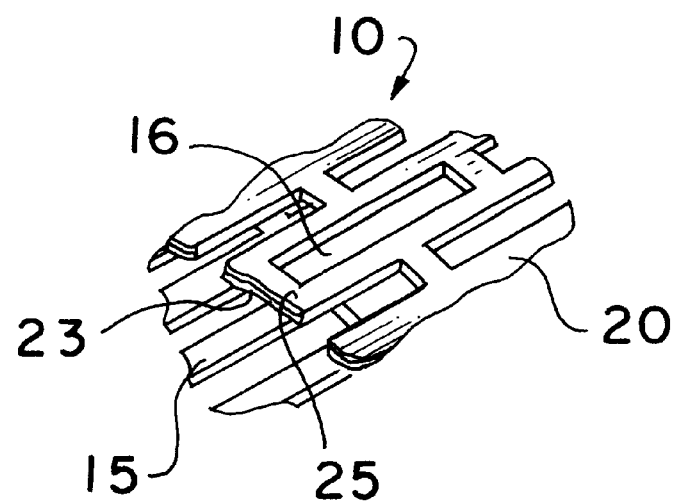
FIG. 2 is a fragmentary enlarged view of the sidewall of the stent of FIG. 1 with a sectioned portion showing detail of the biodegradable coating according to the present invention.

Each layer may incorporate coagulation inhibitors, and may be applied by dipping or spraying the stent in or with a liquid solution of the carrier of moderate viscosity. After each layer (such as 23, 25 of FIG. 2) of coating 20 is applied, the stent is dried before application of the next layer. Particular attention should be given to drying of the final layers above the inner layer which incorporates the radioactive material. It is desirable that the thin, paint-like composite coating should not exceed an overall thickness of 100 microns, and preferably is about 10 microns thick—5 microns for each of the inner layer 23 (radioactive, to inhibit smooth muscle cell proliferation) and outer layer 25 (anticoagulant, to inhibit thrombus formation).

A suitable biodegradable coating solution is prepared by dissolving 480 milligrams (mg) of a drug carrier, such as poly-D, L-lactid (available as R203 of Boehringer Inc., Ingelheim, Germany) in 3 milliliters (ml) of chloroform under aseptic conditions. In principle, however, any biodegradable (or non-biodegradable) coating material that is blood and tissue compatible and can be dissolved, dispersed or emulgated, may be used as the carrier agent if, after application, it undergoes relatively rapid drying to a self-adhesive lacquer- or paint-like coating, and subsequent disintegration in a controlled manner when in contact with the blood or tissue fluids. The molecular weight of 27000 dalton of R203 has been found to best suit the requirements of both mechanical stability and elasticity to guarantee a complete coverage of the stent also in an expanded state.

Sterile active substances may be selectively incorporated in the carrier by addition to the biodegradable carrier solution for antithrombotic, anti-inflammatory, anticoagulant, anti-proliferative and/or antibiotic action. A suitable biodegradable coating material impregnated with hirudin—especially the pharmaceutical preparation of PEG hirudin (polyethylene glycol bound hirudin)—is prepared by dispersing 24 mg of finely separated hirudin power into the carrier solution under aseptic conditions, and then storing the mixture at −10° C. for subsequent application. A liquid hirudin anticoagulant drug solution may be prepared rather than powder.

Other examples of preparation of suitable biodegradable coating compositions incorporating active substances are the following. 48 mg of iloprost (trade name for synthetic prostaglandin derivative) is dispersed under aseptic conditions into the carrier solution, and the composition is stored at −10° C. until ready for use. Prostacyclin $PGI_2$ may be used to substantially the same effect. A dexamethasone coating is prepared by introducing 4.8 mg of finely dispersed dexamethasone powder into the carrier solution. Alternatively, a liquid form of dexamethasone (available under the trade name Fortecortin in Germany), which is crystalline in solution, may be used. For an antibiotic coating, 4.8 mg of gentamicin powder is dispersed into the carrier solution. Heparin can be incorporated as an anticoagulant substance into the coating by dissolving 24 mg of heparin powder into the carrier solution, but is clearly a less favorable antithrombotic agent compared to hirudin for local application.

At times, it may be desired to have a more rapid antithrombotic action, as in cases where a critical infarction patient has a high risk of local thrombus formation by adhesion of preexisting thrombin material to the stent and resultant closure of the coronary artery when the stent is implanted. In such instances, the stent may be coated with a compound including the carrier solution with 50,000 units of urokinase powder incorporated therein, by dipping the stent into the compound solution and then drying the resultant coating on the surface of the stent. Even as such a coated stent is being introduced in the coronary artery, a fast release of the antithrombotic drug is taking place, with controlled biodegradation of the coating, to effect continuous local thrombolysis.

For the inner layer, a suitable amount of the radioactive isotope, such as phosphorous $P^{32}$, is added to the coating carrier to provide a radioactivity level of about one microcurie or somewhat higher level for the overall inner layer, which is deemed to be sufficient to produce the desired inhibition of hyperplasia. Other radioactive materials, including but not limited to an isotope of gold ($Au^{198}$), may alternatively be employed. Because the coating process is performed in the presence of a radioactive material, albeit very low level, the portion of the process involving application of the inner layer to the stent (which, as noted above, may be applied in several thin layers to produce the thicker, preferably 5 micron inner layer) may be and preferably is performed with a robotic apparatus.

Preferably the radioactive material is a beta radiation emitter, and preferably it has a radioactivity half life shorter than the time interval required for the biodegradable carrier to disintegrate, based on the degradation rate of the carrier and the thickness of the overall coating. This would tend to assure that the tissue being treated at the targeted site is subjected to a sufficient dosage of ionizing radiation to inhibit cellular proliferation and the resulting restenosis before the inner layer of carrier material disappears. Moreover, the radioactivity level of the emitter will by then have dissipated to avoid any measurable systemic radioactivity in the patient's body from disintegration of the biodegradable carrier.

As a result of its capability to be expanded in diameter and then to remain relatively rigid, the stent is adapted to prevent elastic recoil of the vessel wall. The carrier portion of the coating is a material having a molecular chain length which renders the it sufficiently elastic on the stent to preclude cracking or other disruption of the coating when the stent is deployed in the vessel. For example, the stent may have a diameter of 0.03 to 0.04 inch when it is in the unexpanded state and crimped onto the balloon catheter, and may be expanded to 2.5 to 5 millimeters when deployed, so that it may be stretched by a factor of 3 to 6. The coating must be sufficiently elastic to preclude it from cracking or becoming brittle during such deployment, that any portion of the stent biomaterial is uncoated and exposed. The R203 material referred to above has a molecular chain length quite adequate for these purposes.

In the coating process, the stent is preferably dipped into the sticky carrier solution (which may be moderately to highly viscous, depending on desired thickness of the coating, or applied in several coats using a spray-on thinner solution) incorporating the selected drug(s), under sterile conditions and at room temperature. Typically, only about 1 to 2 minutes are required for drying. After evaporation of the solvent (e.g., chloroform), the coating tightly adheres to the stent surface. If desired, the coating may be applied to the stent in one or more layers just before the stent is to be implanted. Rather than a premixed solution, the carrier may be supplied separately with mixing instructions and drugs or substances for tailoring the coating with formulas that are individually adjustable and blended by the attending physician.

Although a best mode of practicing the invention by way of certain preferred compositions and methods has been described herein, those skilled in the art will recognize from a consideration of the foregoing description that modifications may be made without departing from the scope of the invention. Accordingly, it is intended that the invention be limited only by the appended claims and applicable principles of law.

What is claimed is:

1. A method of providing a stent with the capability of localized action in placement at a treatment site of an earlier angioplasty procedure for opening the lumen of a blood vessel of a patient, wherein said action is to prevent both thrombus formation on the stent when deployed in the blood vessel and restenosis of the blood vessel attributable to the angioplasty procedure, said method comprising the steps of:

applying as a first layer atop an exposed surface of the stent a coating of a biodegradable carrier which is sufficiently elastic to preclude material disruption of the coating during deployment of the stent, and which undergoes disintegration at a predetermined rate in the presence of blood, having a radioactive substance of relatively low radioactivity level incorporated in said biodegradable carrier to inhibit restenosis, wherein said radioactive substance is selected to have a half life of radioactivity which is not greater than the time interval in which said biodegradable carrier undergoes disintegration, whereby to substantially avoid systemic effect of the radioactive substance on the patient, and applying as a second layer atop said first layer a coating of a biodegradable carrier having an anti-coagulant substance incorporated therein, wherein said anti-coagulant substance is selected to inhibit thrombus formation.

2. The method of claim 1, further including the step of limiting the application of said first and second layers to a composite thickness not to exceed about 100 microns.

3. The method of claim 2, including limiting the composite thickness of said first and second layers not to exceed about 10 microns.

4. The method of claim 3, including applying each of said first and second layers to a thickness of about 5 microns.

5. The method of claim 1, further including the step of drying said first layer for adherence to the stent surface before application of said second layer atop the first layer.

6. The method of claim 1, including selecting Au$^{198}$ as said radioactive substance.

7. The method of claim 1, including selecting a beta radiation emitter as said radioactive substance.

8. The method of claim 7, including selecting phosphorous P$^{32}$ as said beta radiation emitter.

9. The method of claim 1, including selecting hirudin as said anti-coagulant substance.

10. The method of claim 1, including selecting prostaglandin as said anticoagulant substance.

11. A vascular stent for use in conjunction with an angioplasty procedure on a stenosed blood vessel, said stent comprising:

a non-radioactive open-ended biocompatible metallic tube having a sidewall populated with through-holes to allow its diameter to be expanded under sufficient radial force exerted substantially uniformly outward on said sidewall when the stent is to be deployed in the blood vessel, and a relatively dry biodegradable coating overlying and adherent to the overall outer diametric surface of said sidewall, said coating including a biodegradable carrier sufficiently elastic to preclude material disruption of the coating during deployment of the stent, and having a radioactive source material incorporated in said carrier to irradiate at least the inner lining of the vessel wall when the stent is deployed at the site of the angioplasty in said blood vessel, said radioactive source material having a half life which is shorter than the time interval in which said carrier undergoes complete disintegration and an activity level sufficient to deliver a radiation dosage to said inner lining within said time interval to inhibit restenosis of the blood vessel at said angioplasty site, whereby to deliver said radiation dosage and exceed said half life before complete disintegration of said biodegradable coating.

12. The stent of claim 11, wherein the radioactive source material is Au$^{198}$.

13. The stent of claim 11, wherein the radioactive source material is a beta radiation emitter.

14. The stent of claim 13, wherein said radioactive source material is P$^{32}$.

15. The stent of claim 11, wherein said radioactive source material has an activity level of approximately one microcurie.

16. The stent of claim 11, wherein said biodegradable carrier is dry, and said radioactive source material is confined to and relatively uniformly distributed in a first region of said biodegradable coating immediately adjacent the surface of said sidewall and which is thinner than the total thickness of said coating.

17. The stent of claim 16, further including a second region of said biodegradable coating overlying said first region thereof, said second region having an anti-coagulant substance relatively uniformly distributed in said biodegradable carrier.

18. The stent of claim 11, wherein said coating has a composite thickness less than about 100 microns.

19. A stent for implantation at a predetermined site in a body fluid-carrying vessel or duct of a patient's body to inhibit rapid tissue growth in the vicinity of the implant site, said stent comprising an open-ended, non-radioactive metal tubular configuration of preselected length with a pattern of holes through the sidewall thereof to enable radial expansion in response to a force exerted against the inner diameter surface thereof from a compressed state for introduction into the vessel or duct to a deployed expanded state for retention of the outer diameter surface of the stent against the inner lining of the wall of the vessel or duct at the implant site, and a thin elastic coating of a biodegradable carrier material which disintegrates biodegradably over time in the presence of said body fluid overlying and adhered to at least said outer diameter surface of the stent, said coating having a composition adapted to resist cracking during deployment of said stent at said site, and including a radioactive substance carried by said biodegradable carrier material and relatively uniformly distributed therethrough in at least the immediate vicinity of said outer diameter surface along the length of the stent, said radioactive substance having a half life which is shorter than the time interval in which said thin coating of biodegradable carrier material completely disintegrates in said body fluid, whereby to irradiate tissue in the vicinity of said implant site to inhibit tissue proliferation thereat while substantially dissipating the effective level of radioactivity by the time of complete disintegration of said coating to remove the radioactive substance from the locality of the implant site by virtue of flow of said body fluid while avoiding any substantial systemic effect thereof.

20. The stent of claim 19, wherein said vessel or duct is a blood vessel, and said radioactive substance is confined to a first layer of said biodegradable carrier coating immediately adjacent said outer diameter surface of the stent less than the overall thickness of said coating, and further including an anti-coagulant substance relatively uniformly distributed throughout a further layer of said biodegradable carrier coating overlying said first layer, to inhibit thrombus formation on the stent.

21. The stent of claim 20, wherein said biodegradable carrier coating has a thickness of less than approximately 100 microns.

* * * * *